(12) United States Patent
Gilbert

(10) Patent No.: US 8,298,225 B2
(45) Date of Patent: Oct. 30, 2012

(54) SYSTEM AND METHOD FOR RETURN ELECTRODE MONITORING

(75) Inventor: James A. Gilbert, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 785 days.

(21) Appl. No.: 12/407,008

(22) Filed: Mar. 19, 2009

(65) Prior Publication Data

US 2010/0241023 A1 Sep. 23, 2010

(51) Int. Cl.
A61B 18/04 (2006.01)
(52) U.S. Cl. .......................................... 606/35
(58) Field of Classification Search .................... 606/35; 600/547
See application file for complete search history.

(56) References Cited

U.S. PATENT DOCUMENTS

| | | | |
|---|---|---|---|
| 3,471,770 A | 10/1969 | Haire | |
| 3,601,126 A | 8/1971 | Estes | |
| 3,641,422 A | 2/1972 | Farnsworth et al. | |
| 3,923,063 A | 12/1975 | Andrews et al. | |
| 3,952,748 A | 4/1976 | Kaliher et al. | |
| 4,116,231 A * | 9/1978 | Matsuo | 600/547 |
| 4,188,927 A | 2/1980 | Harris | |
| 4,296,413 A | 10/1981 | Milkovic | |
| 4,303,073 A | 12/1981 | Archibald | |
| 4,416,276 A | 11/1983 | Newton et al. | |
| 4,416,277 A | 11/1983 | Newton et al. | |
| 4,438,766 A | 3/1984 | Bowers | |
| 4,494,541 A | 1/1985 | Archibald | |
| 4,559,943 A | 12/1985 | Bowers | |
| 4,586,120 A | 4/1986 | Malik et al. | |
| 4,615,330 A | 10/1986 | Nagasaki et al. | |
| 4,651,280 A | 3/1987 | Chang et al. | |
| 4,818,954 A | 4/1989 | Flachenecker et al. | |
| 4,848,335 A | 7/1989 | Manes | |
| 4,887,199 A | 12/1989 | Whittle | |
| 4,895,169 A | 1/1990 | Heath | |
| 5,061,914 A | 10/1991 | Busch et al. | |
| 5,233,515 A | 8/1993 | Cosman | |
| 5,249,121 A | 9/1993 | Baum et al. | |
| 5,282,840 A | 2/1994 | Hudrlik | |
| 5,300,068 A | 4/1994 | Rosar et al. | |

(Continued)

FOREIGN PATENT DOCUMENTS

CA 1219642 3/1987

(Continued)

OTHER PUBLICATIONS

Moore, Steve. "Charge Injection Compensation Circuits." Designing with Analog Switches. New York: M. Dekker, 1991. 120-22.*

(Continued)

*Primary Examiner* — Michael Peffley
*Assistant Examiner* — Daniel Fowler

(57) ABSTRACT

A detection circuit for return electrode monitoring is disclosed. The detection circuit includes a transformer operatively coupled to a pair of split electrode pads, wherein the transformer is configured to transceive a return electrode sense signal. The detection circuit also includes a first switch coupled to the transformer and a neutrally-referenced second switch, wherein the first switch and the second switch are disposed on a single die. The detection circuit further includes an operational amplifier coupled to the first switch and the neutrally-referenced second switch. The operational amplifier is configured to subtract a noise signal from the return electrode sense signal.

15 Claims, 3 Drawing Sheets

U.S. PATENT DOCUMENTS

| | | |
|---|---|---|
| 5,300,070 A | 4/1994 | Gentelia |
| 5,318,563 A | 6/1994 | Malis et al. |
| 5,472,443 A | 12/1995 | Cordis et al. |
| 5,496,313 A | 3/1996 | Gentelia et al. |
| 5,540,681 A | 7/1996 | Strul et al. |
| 5,540,683 A | 7/1996 | Ichikawa |
| 5,540,684 A | 7/1996 | Hassler, Jr. |
| 5,556,396 A | 9/1996 | Cohen et al. |
| 5,573,533 A | 11/1996 | Strul |
| 5,584,830 A | 12/1996 | Ladd et al. |
| 5,585,756 A | 12/1996 | Wang |
| 5,588,432 A | 12/1996 | Crowley |
| 5,599,347 A | 2/1997 | Hart et al. |
| 5,678,545 A | 10/1997 | Stratbucker |
| 5,733,281 A | 3/1998 | Nardella |
| 5,868,739 A | 2/1999 | Lindenmeier et al. |
| 5,957,961 A | 9/1999 | Maguire et al. |
| 5,999,061 A | 12/1999 | Pope et al. |
| 6,007,532 A | 12/1999 | Netherly |
| 6,032,063 A | 2/2000 | Hoar et al. |
| 6,039,732 A | 3/2000 | Ichikawa et al. |
| 6,055,458 A | 4/2000 | Cochran et al. |
| 6,059,778 A | 5/2000 | Sherman |
| 6,063,075 A | 5/2000 | Mihori |
| 6,093,186 A | 7/2000 | Goble |
| 6,142,992 A | 11/2000 | Cheng et al. |
| 6,171,304 B1 | 1/2001 | Netherly et al. |
| 6,200,314 B1 | 3/2001 | Sherman |
| 6,231,569 B1 | 5/2001 | Bek |
| 6,235,020 B1 | 5/2001 | Cheng et al. |
| 6,246,912 B1 | 6/2001 | Sluijter et al. |
| 6,261,286 B1 | 7/2001 | Goble et al. |
| 6,293,941 B1 | 9/2001 | Strul |
| 6,293,942 B1 | 9/2001 | Goble et al. |
| 6,296,636 B1 | 10/2001 | Cheng et al. |
| 6,306,134 B1 | 10/2001 | Goble et al. |
| 6,310,611 B1 | 10/2001 | Caldwell |
| 6,364,877 B1 | 4/2002 | Goble et al. |
| 6,383,183 B1 | 5/2002 | Sekino et al. |
| 6,391,024 B1 | 5/2002 | Sun et al. |
| 6,402,742 B1 | 6/2002 | Blewett et al. |
| 6,416,509 B1 | 7/2002 | Goble et al. |
| 6,468,270 B1 | 10/2002 | Hovda et al. |
| 6,488,678 B2 | 12/2002 | Sherman |
| 6,497,659 B1 | 12/2002 | Rafert |
| 6,546,270 B1 | 4/2003 | Goldin et al. |
| 6,569,160 B1 | 5/2003 | Goldin et al. |
| 6,575,969 B1 | 6/2003 | Rittman, III et al. |
| 6,632,193 B1 | 10/2003 | Davison et al. |
| 6,652,514 B2 | 11/2003 | Ellman |
| 6,663,623 B1 | 12/2003 | Oyama et al. |
| 6,696,844 B2 | 2/2004 | Wong et al. |
| 6,796,980 B2 | 9/2004 | Hall |
| 6,936,047 B2 | 8/2005 | Nasab et al. |
| 6,939,346 B2 | 9/2005 | Kannenberg et al. |
| 6,962,587 B2 | 11/2005 | Johnson et al. |
| 6,994,707 B2 | 2/2006 | Ellman et al. |
| 7,025,765 B2 | 4/2006 | Balbierz et al. |
| 7,143,926 B2 | 12/2006 | Shelton, IV et al. |
| 7,195,627 B2 | 3/2007 | Amoah et al. |
| 7,211,081 B2 | 5/2007 | Goble |
| 7,238,181 B2 | 7/2007 | Daners et al. |
| 7,250,048 B2 | 7/2007 | Francischelli et al. |
| 7,305,311 B2 | 12/2007 | Van Zyl |
| 7,479,140 B2 | 1/2009 | Ellman et al. |
| 2005/0004634 A1 | 1/2005 | Ricart et al. |
| 2005/0085806 A1 | 4/2005 | Auge, II et al. |
| 2005/0101947 A1* | 5/2005 | Jarrard et al. ............ 606/35 |
| 2007/0173804 A1 | 7/2007 | Wham et al. |
| 2007/0173806 A1 | 7/2007 | Orszulak et al. |
| 2007/0203481 A1 | 8/2007 | Gregg et al. |
| 2008/0125767 A1 | 5/2008 | Blaha |
| 2008/0281309 A1 | 11/2008 | Dunning et al. |
| 2009/0157071 A1 | 6/2009 | Wham et al. |
| 2009/0157072 A1 | 6/2009 | Wham et al. |
| 2009/0157075 A1 | 6/2009 | Wham et al. |

FOREIGN PATENT DOCUMENTS

| | | |
|---|---|---|
| DE | 3239640 | 5/1983 |
| DE | 3206947 | 9/1983 |
| DE | 3544443 | 6/1987 |
| DE | 4238263 | 5/1993 |
| DE | 4231236 | 3/1994 |
| DE | 19717411 | 11/1998 |
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 694291 | 1/1996 |
| EP | 836868 | 4/1998 |
| EP | 0930048 | 7/1999 |
| EP | 1051949 | 11/2000 |
| EP | 1076350 | 2/2001 |
| EP | 1293171 | 3/2003 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| FR | 2276027 | 6/1974 |
| FR | 2516782 | 5/1983 |
| GB | 2054382 | 2/1981 |
| GB | 2374532 | 10/2002 |
| WO | WO95/19148 | 7/1995 |
| WO | WO98/27880 | 7/1998 |
| WO | WO 99/11187 | 3/1999 |
| WO | WO 99/98999 | 3/1999 |
| WO | WO 00/65993 | 11/2000 |
| WO | WO02/47565 | 6/2002 |
| WO | WO 2004028385 | 4/2004 |
| WO | WO2005/048809 | 6/2005 |
| WO | WO2005/050151 | 6/2005 |
| WO | WO 2005/087124 | 9/2005 |
| WO | WO 2005/115262 | 12/2005 |
| WO | WO 2008/009385 | 1/2008 |

OTHER PUBLICATIONS

European Search Report EP 10157054 dated Sep. 21, 2010.
U.S. Appl. No. 10/609,946, filed Jun. 30, 2003.
U.S. Appl. No. 11/900,190, filed Sep. 10, 2007.
U.S. Appl. No. 12/396,814, filed Mar. 3, 2009.
U.S. Appl. No. 12/395,812, filed Mar. 2, 2009.
U.S. Appl. No. 12/364,624, filed Feb. 3, 2009.
U.S. Appl. No. 12/355,281, filed Jan. 16, 2009.
U.S. Appl. No. 12/401,428, filed Mar. 10, 2009.
U.S. Appl. No. 12/407,008, filed Mar. 19, 2009.
Boyles, Walt; "Instrumentation Reference Book", 2002; Butterworth-Heinemann ; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
International Search Report PCT/US2004/004196 dated Oct. 4, 2007.

* cited by examiner

SYSTEM AND METHOD FOR RETURN ELECTRODE MONITORING

BACKGROUND

1. Technical Field

The present disclosure relates to electrosurgical apparatuses, systems and methods. More particularly, the present disclosure is directed to electrosurgical systems configured to monitor contact quality of return electrode pads to the patient during electrosurgical procedures.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode.

The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive gel. Later, adhesive electrodes were developed with a single metal foil covered with conductive gel or conductive adhesive. However, one problem with these adhesive electrodes was that if a portion peeled from the patient, the contact area of the electrode with the patient decreased, thereby increasing the current density at the adhered portion and, in turn, increasing the heating at the tissue. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on measuring impedance at the return electrode to calculate a variety of tissue and/or electrode properties. These systems detected peeling by identifying changes in impedance of the return electrodes.

SUMMARY

According to one embodiment of the present disclosure, a detection circuit for return electrode monitoring is disclosed. The detection circuit includes a transformer operatively coupled to a pair of split electrode pads, wherein the transformer is configured to transceive a return electrode sense signal. The detection circuit also includes a first switch coupled to the transformer and a neutrally-referenced second switch, wherein the first switch and the second switch are disposed on a single die. The detection circuit further includes an operational amplifier coupled to the first switch and the neutrally-referenced second switch. The operational amplifier is configured to subtract a noise signal from the return electrode sense signal.

According to another embodiment of the present disclosure, a return electrode monitoring system is disclosed. The system includes a return electrode pad including one pair of split electrode pads and a detection circuit having a transformer operatively coupled to the pair of split electrode pads, wherein the transformer is configured to transceive a return electrode sense signal. The detection circuit also includes a first switch coupled to the transformer and a neutrally-referenced second switch, wherein the first switch and the second switch are disposed on a single die and generate substantially similar switch noise signals. The system also includes an operational amplifier coupled to the at least one first switch and the at least one neutrally-referenced second switch. The operational amplifier configured to cancel out the switch noise signals from the return electrode sense signal.

According to a further embodiment of the present disclosure a return electrode monitoring system is disclosed. The system includes a return electrode pad having one or more pairs of split electrode pads and a detection circuit having a single-ended primary transformer operatively coupled to the pair of split electrode pads, wherein the single-ended primary transformer is configured to transceive a return electrode sense signal. The detection circuit also includes a switch package including a first switch coupled to the single-ended primary transformer and a neutrally-referenced second switch, wherein the first switch and the second switch generate substantially similar switch noise signals. The detection circuit also includes an operational amplifier coupled to the switch package. The operational amplifier is configured to subtract the switch noise signals from the return electrode sense signal. The system also includes a controller coupled to the detection circuit and configured to analyze the noise-cancelled return electrode sense signal.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
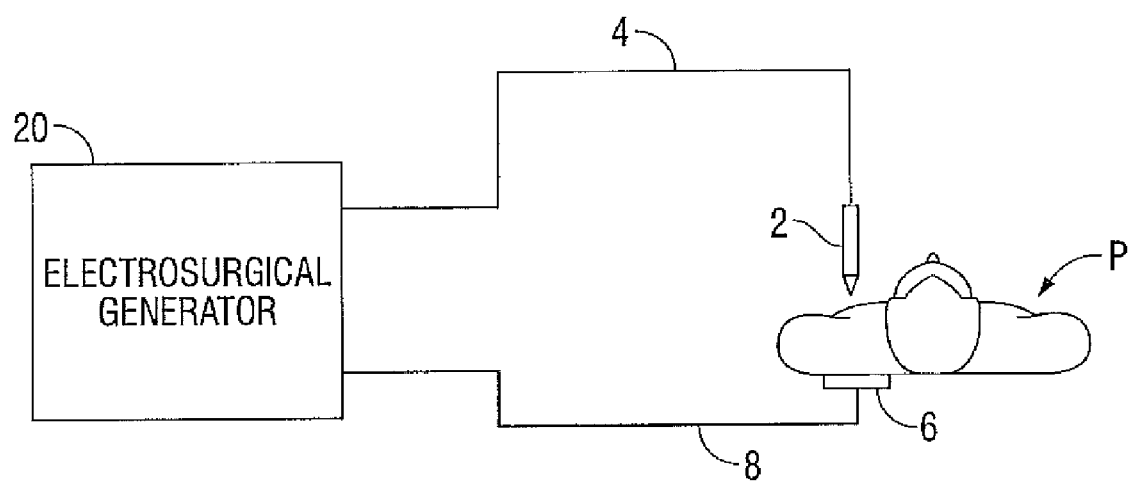
FIG. 1 is a schematic block diagram of an electrosurgical system according to one embodiment of the present disclosure.

FIG. 1 is a schematic illustration of an electrosurgical system according to one embodiment of the present disclosure. The system includes an electrosurgical instrument 2, which is a monopolar instrument including one or more active electrodes (e.g., electrosurgical cutting probe, ablation electrode(s), etc.) for treating tissue of a patient P. Electrosurgical RF energy is supplied to the instrument 2 by a generator 20 via an electrosurgical cable 4 connected to an active output terminal that allows the instrument 2 to coagulate, ablate and/or otherwise treat tissue. The energy is returned to the generator 20 through a return electrode pad 6 via a return cable 8. The system may include a plurality of return electrodes pads 6 arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

The generator 20 may include input controls (e.g., buttons, activators, switches, touch screen, etc.) for controlling the generator 20. In addition, the generator 20 may include one or more display screens for providing the user with variety of output information (e.g., intensity settings, treatment complete indicators, etc.) The input controls allow the user to adjust power of the RF energy, waveform, and other parameters to achieve the desired electrosurgical output suitable for a particular task (e.g., coagulating, cauterizing, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2:
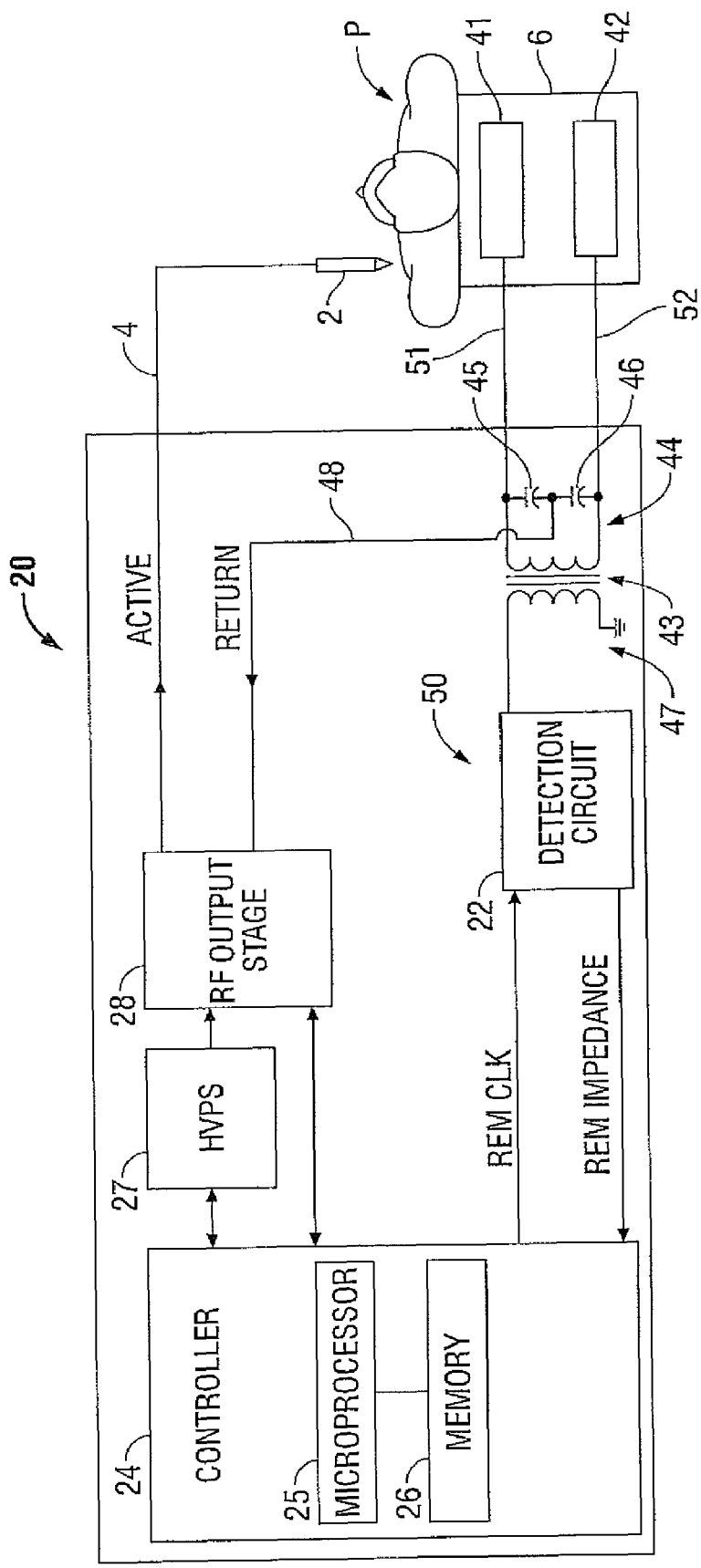
FIG. 2 is a schematic block diagram of a generator according to an embodiment of the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28, which then converts high voltage DC power into RF energy and delivers the RF energy to the active electrode. In particular, the RF output stage 28 generates suitable waveforms of high RF energy. The RF output stage 28 is configured to generate a plurality of waveforms having various duty cycles, peak voltages, crest factors, and other parameters.

The controller 24 includes a microprocessor 25 operably connected to a memory 26, which may be volatile type memory (e.g., RAM) and/or non-volatile type memory (e.g., flash media, disk media, EPROM, etc.). The microprocessor 25 includes an output port that is operably connected to the HVPS 27 and/or RF output stage 28 that allows the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

The generator 20 includes a return electrode monitoring ("REM") system 50 having a detection circuit 22 which is coupled to a pair of split electrode pads, a first electrode pad 41 and a second electrode pad 42 disposed within the return electrode pad 6. The return electrode pad 6 is in contact with the patient P and returns the electrosurgical energy to the generator 20 via the first and second electrode pads 41 and 42 coupled to leads 51 and 52, respectively. In one embodiment, the return electrode pad 6 may include a plurality of split electrode pads arranged in pairs that are coupled to a corresponding number of leads. The leads 51 and 52 are enclosed in a return cable 8 and are terminated at a secondary winding 44 of a transformer 43. The leads 51 and 52 are interconnected by capacitors 45 and 46. A return lead 48 is coupled between the capacitors 45 and 46 and is adapted to return the electrosurgical energy to the RF output stage 28. The transformer 43 of the REM system 50 also includes a primary winding 47 that is connected to the detection circuit 22.

The controller 24 provides a drive signal, REM CLK, at a specific interrogation frequency to the detection circuit 22. REM CLK, is a clock signal generated by the controller 24 at the specific frequency, which may be either a square wave, a sine wave, an impulse or step signal. REM CLK may be a constant, physiologically benign waveform (e.g., 140 kHz, 2 mA) that the detection circuit 22 applies to the first electrode pad 41. The drive signal thereafter passes through the patient and is returned to the circuit 22 via the second electrode pad 42. The detection circuit 22 then measures a response signal to the drive signal and monitors the changes in the response signal to determine degree of adhesion of the return electrode pad 6.

The response signal (e.g., returning drive signal) is modified by the impedance of the first and second electrode pads 41 and 42. More specifically, as the impedance between the split electrode pads 41 and 42 changes due to peeling of the return electrode pad 6 from the patient the detection circuit 22 then supplies the impedance measurement to the controller 24, which determines whether the impedance is within a desired range. If the impedance is outside the desired range an excessive peeling condition exists with the return electrode pad 6 and the controller 24 issues an alarm and/or adjusts the output of the generator 20 (e.g., terminates RF energy supply).

Figure 3:
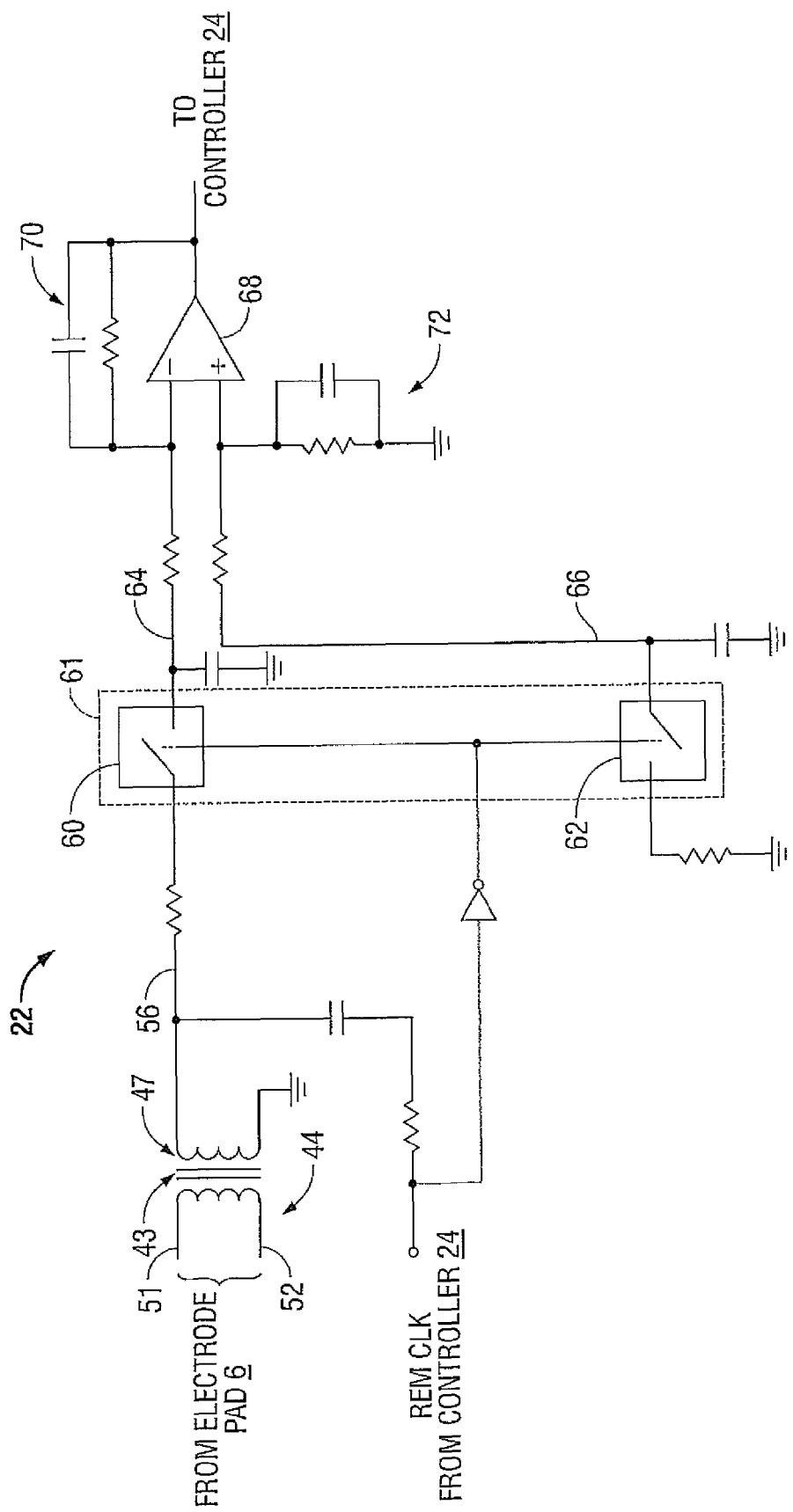
FIG. 3 is a schematic circuit diagram of a detection circuit according to an embodiment of the present disclosure.

With reference to FIG. 3, the detection circuit 22 is coupled to the primary winding 47 of the transformer 43 and the secondary winding 44 is coupled to the return electrode pad 6. The primary winding 47 is in a single-ended primary configuration, in which the primary winding 47 is referenced to the ground and includes a single-ended line 56. The primary winding 47 is also coupled to an input from the controller 24 for transmitting the REM CLK signal therethrough.

The detection circuit 22 also includes a first switch 60 and a second switch 62 that are operated by the REM CLK. The first and second switches 60 and 62 are analog switches disposed on the same switch package 61 (e.g., being disposed on a single die). The first switch 60 is coupled to the single-ended line 56 of the primary winding 47. The switches 60 and 62 are operated at the REM CLK frequency. When the first switch 60 is open the REM sense signal from the electrode pad 6 is transmitted therethrough to the controller 24. The second switch 62 is neutrally-referenced to a ground and when the second switch 62 is open, only the noise introduced by charge injection is produced. The first and second switches 60 and 62 may be transistors, such as complementary metal-oxide-semiconductor field-effect transistors (CMOS), metal-oxide-semiconductor field-effect transistors (MOSFET), junction field-effect transistors (JFET) and the like.

When the first and second switches 60 and 62 are operated, a small electric charge, so-called "charge injection," is introduced into the signal when the switch is closed. Thus, the REM sense signal from the return electrode pad 6 is contaminated by the noise from the charge injection of the first switch 60. Charge injection is not a desirable feature of analog switches as manufacturers are always striving to reduce its effect. However, during analog switch manufacture, charge injection is not a well-controlled process parameter, making it difficult to produce switches having specific charge injection. Calibration for specific charge injection is also problematic. Manufacturers may modify the charge injection parameters of the switches without notice, e.g., due to a change in manufacturing process, which requires recalibration to account for the change in the charge injection. However, if a package or die including multiple switches is used, the charge injection across the switches of that package is substantially similar. Without being restricted by a particular theory, it is believed that having two corresponding switches, e.g., first and second switches 60 and 62, being disposed on the same switch package 61 provides for switches that share substantially similar operating characteristics, such as charge injection.

The present disclosure provides for a system for elimination of noise from the REM sense signal as transmitted through the first switch 60. Since the noise produced by the first and second switches 60 and 62 is the same, the noise component may be canceled by differentiating the noisy neutrally-referenced signal from the noisy REM sense signal (e.g., having switch noise). More specifically, since the second switch 62 is neutrally-referenced, the signal produced therefrom includes only the noise component.

In one embodiment of the present disclosure, the switch package 61 having the first and second switches 60 and 62 is disposed on a single die eliminates the noise. The first and second switches 60 and 62 are coupled via lines 64 and 66, respectively, to a differential amplifier 68. The differential amplifier 68 may be any type of an averaging operational amplifier. In particular, the signals from the first and second switches 60 and 62 are applied to RC circuits 70 and 72, respectively. Each of the RC circuits 70 and 72 include a resistor and a capacitor connected in parallel. The RC circuits 70 and 72 connected in this manner provide an integrating or an averaging function that converts the AC REM sense signal into a proportional DC signal. The signals appearing across the RC circuits 70 and 72 are then applied to the differential amplifier 68, which subtracts the noisy neutrally references signal from the second switch 62 from the noisy REM sense signal from the first switch 60, thereby canceling out the noise signals. Since the first and second switches 60 and 62 are disposed on the same die the noise component is the same in each of the signals, the differential amplifier 68 outputs a noise-cancelled REM sense signal. The REM signal is transmitted to the controller 24, which determines whether the DC voltage (e.g., from the RC circuits 70 and 72) that is proportional to the REM impedance is within a predetermined range. If the impedance is outside the predetermined range, an excessive peeling condition exists and the controller 24 issues an alarm and/or adjusts the output of the generator 20 (e.g., terminates RF energy supply).

In one embodiment, the detection circuit 22 may include a plurality of first switches 60 and a plurality of corresponding second switches 62. In this embodiment, the pairs of first and second switches 60 and 62 may be disposed on the same switch package 61 as shown in FIG. 3 or alternatively, multiple first and corresponding switches 60 and 62, e.g., four switches, with two pairs of switches 60 and 62, may be disposed on the same switch package 61.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A detection circuit for return electrode monitoring, the detection circuit comprising:
   a transformer including a primary winding and a secondary winding, wherein the secondary winding is operatively coupled to at least one pair of split electrode pads;
   a controller coupled to the transformer and configured to output a return electrode sense signal to the at least one pair of split electrode pads;
   at least one first switch coupled to the primary winding and the controller;
   at least one neutrally-referenced second switch coupled to the controller, wherein the at least one first switch and the at least one neutrally-referenced second switch are disposed on a single die and are configured to activate in response to the return electrode sense signal; and
   an operational amplifier coupled to the at least one first switch and the at least one neutrally-referenced second switch, the operational amplifier being configured to subtract a noise signal from the return electrode sense signal, wherein the controller is configured to analyze the noise-cancelled return electrode sense signal.

2. A detection circuit according to claim 1, wherein the transformer is a single-ended primary transformer.

3. A detection circuit according to claim 1, wherein the at least one first switch and the at least one neutrally-referenced second switch are selected from a group consisting of complementary metal-oxide-semiconductor field-effect transistors, metal-oxide semiconductor field-effect transistors, and insulated gate bipolar transistors.

4. A detection circuit according to claim 1, wherein a charge injection parameter of each of the at least one first switch and the at least one neutrally-referenced second switch is substantially similar.

5. A detection circuit according to claim 1, wherein the detection circuit further includes a first RC circuit coupled to the at least one first switch and the operational amplifier and a second RC circuit coupled to the at least one neutrally-referenced second switch and the operational amplifier.

6. A return electrode monitoring system comprising:
   at least one return electrode pad including at least one pair of split electrode pads;
   a detection circuit including:
      a transformer including a primary winding and a secondary winding, wherein the secondary winding is operatively coupled to the at least one pair of split electrode pads;
      a controller coupled to the transformer and configured to output a return electrode sense signal to the at least one pair of split electrode pads;
      at least one first switch coupled to the primary winding and the controller;
      at least one neutrally-referenced second switch coupled to the controller, wherein the at least one first switch and the at least one neutrally-referenced second switch are disposed on a single die and are configured to activate in response to the return electrode sense signal and to generate substantially similar noise signals; and
      an operational amplifier coupled to the at least one first switch and the at least one neutrally-referenced second switch, wherein the operational amplifier is configured to cancel out the noise signals from the return electrode sense signal, wherein the controller is configured to analyze the noise-cancelled return electrode sense signal.

7. A return electrode monitoring system according to claim 6, wherein the transformer is a single-ended primary transformer.

8. A return electrode monitoring system according to claim 6, wherein the at least one first switch and the at least one neutrally-referenced second switch are selected from a group consisting of complementary metal-oxide-semiconductor field-effect transistors, metal-oxide semiconductor field-effect transistors, and insulated gate bipolar transistors.

9. A return electrode monitoring system according to claim 6, wherein a charge injection parameter of each of the at least one first switch and the at least one neutrally-referenced second switch is substantially similar.

10. A return electrode monitoring system according to claim 6, wherein the detection circuit further includes a first RC circuit coupled to the at least one first switch and the operational amplifier and a second RC circuit coupled to the at least one neutrally-referenced second switch and the operational amplifier.

11. A return electrode monitoring system comprising:
at least one return electrode pad including at least one pair of split electrode pads;
a detection circuit including:
- a single-ended primary transformer including a primary winding and a secondary winding, wherein the secondary winding is operatively coupled to the at least one pair of split electrode pads;
- a controller coupled to the transformer and configured to output a return electrode sense signal to the at least one pair of split electrode pads;
- a switch package including at least one first switch coupled to the primary winding and at least one neutrally-referenced second switch each of which is coupled to the controller, wherein the at least one first switch and the at least one neutrally-referenced second switch generate substantially similar noise signals and are configured to activate in response to the return electrode sense signal; and
- an operational amplifier coupled to the switch package, wherein the operational amplifier is configured to cancel out the noise signals from the return electrode sense signal and the controller is configured to analyze the noise-cancelled return electrode sense signal.

12. A return electrode monitoring system according to claim 11, wherein the at least one first switch and the at least one neutrally-referenced second switch are selected from the group consisting of complementary metal-oxide-semiconductor field-effect transistors, metal-oxide semiconductor field-effect transistors, and insulated gate bipolar transistors.

13. A return electrode monitoring system according to claim 11, wherein the at least one first switch and the at least one neutrally-referenced second switch are disposed on a single die of the switch package.

14. A return electrode monitoring system according to claim 11, wherein a charge injection parameter of each of the at least one first switch and the at least one neutrally-referenced second switch is substantially similar.

15. A return electrode monitoring system according to claim 11, wherein the detection circuit further includes a first RC circuit coupled to the at least one first switch and the operational amplifier and a second RC circuit coupled to the at least one neutrally-referenced second switch and the operational amplifier.

* * * * *